United States Patent [19]
Lavagnino et al.

[11] 3,932,435
[45] Jan. 13, 1976

[54] PREPARATION OF N-2-(6-HYDROXYBENZOTHIAZOLYL)-N'-PHENYL (OR SUBSTITUTED-PHENYL) UREAS

[75] Inventors: Edward R. Lavagnino; Charles J. Paget, both of Indianapolis; James H. Wikel, Greenwood, all of Ind.

[73] Assignee: Eli Lilly and Company, Indianapolis, Ind.

[22] Filed: Aug. 30, 1974

[21] Appl. No.: 502,130

[52] U.S. Cl. ............................................. 260/305
[51] Int. Cl.² ...................................... C07D 277/82
[58] Field of Search ................................... 260/305

[56] References Cited
OTHER PUBLICATIONS
Dyer et al., J. Am. Chem. Soc., 81, 2138–2143 (1959).

Smith, The Chemistry of Open–Chain Organic Nitrogen Compounds, Vol. I. N.Y., Benjamin, 1965, p. 270.

Primary Examiner—R. Gallagher
Attorney, Agent, or Firm—James L. Rowe; Everet F. Smith

[57] ABSTRACT

N-2-(6-hydroxybenzothiazolyl)-N'-phenyl (or substituted-phenyl) ureas are prepared by reacting 2-amino-6-hydroxybenzothiazole with 1–2 moles of phenyl (or a substituted phenyl) isocyanate and then hydrolysing any 6-phenylcarbamoyloxy compound thus produced to the corresponding 6-hydroxy derivative.

1 Claim, No Drawings

PREPARATION OF N-2-(6-HYDROXYBENZOTHIAZOLYL)-N'-PHENYL (OR SUBSTITUTED-PHENYL) UREAS

BACKGROUND OF THE INVENTION

Heterocyclic ureas such as N-benzimidazolyl, N-benzothiazolyl or N-benzoxazolyl-N'-phenyl ureas are useful as immune regulants and anti-viral compounds according to Paget et al., J. Med. Chem., 12, 1010 (1969); 1016 (1969). These N-heterocyclic-N'-phenyl ureas can be substituted in either the phenyl moiety of the heterocyclic benzothiazole, benzoxazole or benzimidazole ring with substituents such as halo, alkoxy, alkyl, carboethoxy, trifluoromethyl, nitro and the like, or in the N'-phenyl group with substituents such as chloro, fluoro, nitro, methyl, trifluoromethyl, bromo and the like. Compounds which contain a hydroxy group as a substituent in the phenyl portion of the heterocyclic nucleus have not been prepared. Obvious methods of preparing such a 6-hydroxy derivative have been found not to be operative; for example, the corresponding 6-methoxy compound is not readily demethylated by the use of 50 percent HBr or other standard demethylating reagent. In addition, carrying out the standard synthesis of benzimidazolyl, benzoxazolyl or benzothiazolyl ureas involving the reaction of an isocyanate with a 2-amino-substituted benzimidazole, benzoxazole or benzothiazole, having a benzyloxy substituent in the phenyl moiety of the heterocyclic ring also did not provide an operative procedure for preparing the corresponding hydroxy compound since the benzyl group proved to be extremely resistant to debenzylation using hydrogenation conditions involving a palladium catalyst. N-2-(6-hydroxybenzothiazolyl)-N'-phenyl urea was, however, discovered as a metabolic product in urine when the corresponding 6-methoxy compound was fed to rats. A complex procedure for preparing this compound involving the use of trimethylsilyl chloride has been devised, as fully set forth in the copending application of Paget and Wikel, Ser. No. 502,129 filed this even date.

It is an object of this invention to provide an improved method for preparing N-2-(6-hydroxybenzothiazolyl)-N'-phenyl (or substituted-phenyl) ureas, which improved method is more adaptable to industrial production than methods heretofore available and which avoids the use of expensive reagents.

SUMMARY OF THE INVENTION

In fulfillment of the above and other objects, this invention provides a method for the preparation of N-2-(6-hydroxybenzothiazolyl)-N'-phenyl (or substituted phenyl) ureas represented by formula I below which comprises the reaction of 1–2 moles (up to a 100 percent molar excess) of a phenylisocyanate (R'—C$_6$H$_4$—NCO) with 2-amino-6-hydroxybenzothiazole to produce a reaction mixture containing a 6-carbamoyloxy derivative (structure II) and permissably, some of the compound of structure I below.

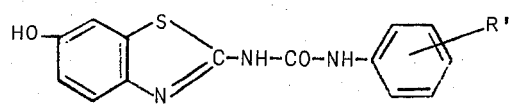

I

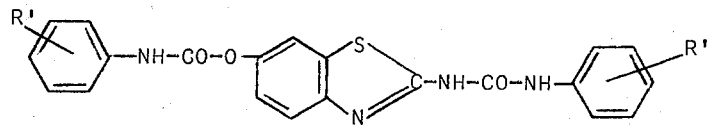

II

The N-2-(6-phenylcarbamoyloxybenzothiazolyl)-N'-phenyl urea (II) thus produced is treated with base in an inert solvent at a temperature below about 100°C. until all of the 6-phenylcarbamoyloxy group of the benzothiazolyl urea has been hydrolyzed to provide a compound of structure I. The 6-phenylcarbamoyl compound produced in the isocyanate reaction can be hydrolyzed to the 6-hydroxy derivative either in the original reaction mixture or during an initial separation step wherein advantage is taken of the phenolic character of the 6-hydroxy group to dissolve it in base. The base-insoluble compound is separated and then hydrolyzed by the process of this invention. It is, of course, preferable to carry out the hydrolysis step in the unseparated reaction mixture. The 6-hydroxy urea (I) already present or produced by the hydrolytic reaction is not adversely affected under the specified hydrolysis reaction conditions.

In structures I and II above, R' is the same group in each instance and can be hydrogen, halo, (C$_1$–C$_3$) alkyl or (C$_1$–C$_3$) alkyloxy. The term "(C$_1$–C$_3$) alkyl" includes methyl, ethyl, n-propyl and isopropyl. Thus, the term "(C$_1$–C$_3$) alkyloxy" includes methoxy, ethoxy, n-propoxy and isopropoxy. The term "halo" includes fluoro, chloro, bromo and iodo.

In the reaction between the phenylisocyanate (R'—C$_6$H$_4$—NCO) and the 2-amino-6-hydroxybenzothiazole, the 2-amino group of the benzothiazolyl reacts far more rapidly than does the 6-hydroxy group. Thus, with a single mole of phenylisocyanate, the predominant reaction product will be N-2-(6-hydroxybenzothiazolyl)-N'-phenyl urea. The reaction between the hydroxy group and the phenylisocyanate does, however, proceed at a measurable reaction rate. Using only a single mole of isocyanate, therefore, the chief reaction product will be the urea of structure I, as stated above but there will also be present 2-amino-6-carbamoyloxybenzothiazole, N-2-(6-carbamoyloxybenzothiazolyl)-N'-phenyl urea and unreacted 2-amino-6-hydroxybenzothiazol starting material. Sufficient phenylisocycnate or substituted phenylisocyanate should be employed to insure that all of the 2-amino group of the benzothiazole reacts to form the corresponding urea, and preferably, a stoichiometric excess from about 25–100 percent of the isocyanate is employed. A greater than 100 percent stoichiometric excess (2 moles per mole of amino benzothiazole) is, of course, not necessary since with 2 moles of phenyl (or a substituted-phenyl) isocyanate present, all of the benzothiazole will be converted to the 6-carbamoyloxy urea (structure II above). If less than 2 moles, but more than 1 mole, of isocyanate is used per mole of benzothiazole, the reaction mixture will contain both the 6-hydroxy and 6-carbamoyloxy derivatives. In any case, in order to obtain a substantially quantitative yield of the desired 6-hydroxy compound, it is necessary to hydrolyze any 6-carbamoyloxy derivative produced in the isocyanate reaction using base in an inert solvent at a temperature below about 100°C. until substantially all of the 6-carbamoyloxy group is hydrolyzed to the desired 6-hydroxy compound of structure I above. Useful inert solvents include water and the lower alkanols including methanol and ethanol. Suitable bases for use in the process include alkali metal hydroxides such as potassium or sodium hydroxide; alkali metal alcoholates such as potassium ethylate, sodium methylate and the like; alkali metal carbonates including potassium and sodium carbonate; and ammonium hydroxide, and substituted ammonium hydroxides such as triethyl ammonium hydroxide, trimethyl ammonium hydroxide and the like. The temperature of the reaction is customarily carried out at the reflux temperature of the solvent; i.e., from 65°C. for methanol to 100°C. for water. As will be apparent to those skilled in the art, the higher the reflux temperature, the shorter the time needed for the hydrolysis to proceed to completion. Likewise, the solubility of the base in the inert solvent in an important consideration with the alkali metal hydroxides, for example, being more soluble than the carbonates. Use of the hydroxides therefore requires less reaction time than use of the carbonates. Complete hydrolysis of the 6-phenylcarbamoyloxy compound usually requires from 1 to about 18 hours depending upon solvent, base and temperature employed, and upon the nature of the 6-phenyl (or substituted-phenyl) carbamoyloxy group.

The character of the isocyanate (R'—C$_6$H$_4$—NCO) affects not only the rate of hydrolysis of the 6-phenyl (or substituted-phenyl) carbamoyloxy group as indicated above, but also affects the ratios of the various products of the reaction of the particular isocyanate with 2-amino-6-hydroxybenzothiazole, specially the rate of urea formation compared to the rate of reaction with the 6-hydroxy group.

N-2-(6-hydroxybenzothiazolyl)-N'-phenyl urea and other substituted phenyl ureas represented by formula I above are useful as anti-viral agents and as immune suppressants, as set forth in the copending application of Paget and Wikel, Ser. No. 502,129 filed this even day.

The preparation of N-2-(6-hydroxybenzothiazolyl)-N'-phenyl urea is illustrated in the examples which follow with Examples 2–6 describing alternate methods of hydrolyzing the 6-phenylcarbamoyloxy group.

EXAMPLE 1

A slurry of 152 g. of 2-amino-6-hydroxybenzothiazole was prepared in 3 liters of acetone. A solution of 109 g. of phenylisocyanate in 150 ml. of acetone was added thereto in dropwise fashion. After the addition had been completed, the reaction mixture was heated at refluxing temperature overnight. The reaction mixture was cooled to about 50°C. and decolorizing charcoal added. The mixture was filtered, and a second batch of 109 g. of phenylisocyanate in acetone added to the filtrate. The mixture was again heated to refluxing temperature for about 2 hours, and was cooled. A white solid comprising N-2-(6-phenyl-carbamoyloxybenzothiazolyl)-N'-phenyl urea formed in the above reaction precipitated. The precipitate was separated by filtration, and the filter cake washed with acetone. Yield = 73 percent. Melting point above 250°C.

Analysis for $C_{21}H_{15}N_4O_3S$: Calc.: C, 62.52; H, 3.75; N, 13.89; S, 7.95; Found: C, 62.30; H, 3.97; H, 13.69; S, 7.76.

Four grams of the above N-2-(6-carbamoyloxybenzothiazolyl)-N'-phenyl urea were dissolved in 150 ml. of anhydrous methanol. A 10 percent slurry of 0.5 g. of sodium methylate in methanol was added with stirring. The reaction mixture was stirred at room temperature overnight. Thin layer chromatography showed that about 50 percent of the carbamoyloxy group had been removed by hydrolysis. The reaction mixture was then slowly heated, and the progress of the reaction continually checked by thin layer chromatography. After two hours of heating at about 45°C., the hydrolysis was substantially 100 percent complete. The reaction mixture was then cooled and carefully acidified to pH = 4 with 10 percent aqueous hydrochloric acid. N-2-(6-hydroxybenzothiazolyl)-N'-phenyl urea formed in the above reaction was separated by filtration. The filter cake was washed with methanol and then ether. Examination of its NMR spectra indicated that a phenyl-carbamoyloxy group was no longer present in the molecule. This fact was further substantiated by shifts in the ultraviolet spectrum upon solution of the compound in acid and base. N-2-(6-hydroxybenzothiazolyl)-N'-phenyl urea thus prepared had the following characteristics: m.p. above 250°C.; mass spectral fragments at 285,212, 192, and 166; pKa = 10.9 (66% DMF).

Analysis Calc. for $C_{14}H_{11}N_3O_2S$: C, 58.93; H, 3.89; N, 14.73; Found: C, 58.34; H, 3.76; N, 13.76.

EXAMPLE 2

A reaction mixture was prepared containing 100 mg. of N-2-(6-phenylcarbamoyloxybenzothiazolyl)-N'-phenyl urea, 100 mg. of sodium methylate and 25 ml. of methanol. The reaction mixture was refluxed for one-half hour, at the end of which time thin layer chromatography indidcated that none of the starting material was present and that the product of the reaction was the corresponding 6-hydroxy compound. Further refluxing of the reaction mixture for 18 hours showed no decomposition of N-2-(6-hydroxybenzothiazolyl)-N'-phenyl urea formed in the reaction.

EXAMPLE 3

Example 2 was repeated except that 20 mg. of potassium hydroxide were substituted for the sodium methylate of that example. An examination of the reaction mixture by thin layer chromatography after 6 hours indicated that the hydrolysis of the 6-phenyl-carbamoyloxy group was incomplete. Refluxing was continued for another 12 hours, at the end of which time it was ascertained that hydrolysis was complete and that the starting material had been entirely converted to the corresponding 6-hydroxy compound.

EXAMPLE 4

The procedure of Example 1 was repeated except that about 35 mg. of potassium carbonate were employed in place of the sodium methylate of that example. Examination of the reaction mixture at intervals indicated that 18 hours were required to hydrolyze completely the 6-phenylcarbamoyloxy group.

EXAMPLE 5

The procedure of Example 3 was repeated except that 25 ml. of water were employed in place of the methanol of that example. The reaction mixture was heated slowly, and the solid starting material went into solution at about 80°C. Refluxing for 1 hour gave complete hydrolysis of the 6-phenylcarbamoyloxy group.

EXAMPLE 6

The procedure of Example 2 was repeated except that 0.35 ml. of triethylamine were used in place of the sodium methylate of that example. Examination by thin layer chromatography indicated that the hydrolysis was complete after a 6-hour reflux.

We claim:
1. The process which comprises the essential steps
   1. reacting 2-amino-6-hydroxy-benzothiazole with from 1-2 moles of a phenyl isocyanate of the formula

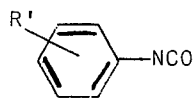

wherein R' is H, $(C_1-C_3)$ alkyl, $(C_1-C_3)$ alkoxy or halo;
   2. hydrolyzing any thus-obtained 6-carbamoyloxy compound of the formula

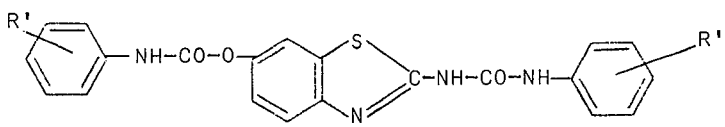

wherein R' has the same meaning as hereinabove; with a base of the group comprising alkali metal hydroxides, and carbonates, ammonium hydroxide and $(C_1-C_2)$ alkyl-substituted ammonium hydroxides in an inert solvent at a temperature not higher than about 100°C. until the 6-carbamoyloxy derivative is converted substantially completely to the corresponding 6-hydroxy derivative of the formula wherein R' has the same meaning as hereinabove; and then
   3. isolating said 6-hydroxy derivative.

* * * * *